United States Patent [19]

Farng et al.

[11] Patent Number: 5,137,649
[45] Date of Patent: * Aug. 11, 1992

[54] MIXED ALCOHOL/DIMERCAPTOTHIADIAZOLE-DERIVED HYDROXY BORATES AS ANTIOXIDANT/ANTIWEAR MULTIFUNCTIONAL ADDITIVES

[75] Inventors: Liehpao O. Farng, Lawrenceville; Andrew G. Horodysky; William F. Olszewski, both of Cherry Hill, all of N.J.

[73] Assignee: Mobil Oil Corporation, Fairfax, Va.

[ * ] Notice: The portion of the term of this patent subsequent to Mar. 6, 2007 has been disclaimed.

[21] Appl. No.: 489,429

[22] Filed: Mar. 6, 1990

[51] Int. Cl.$^5$ ............... C10M 139/00; C10M 135/36
[52] U.S. Cl. .................... 252/46.3; 548/142
[58] Field of Search .............. 252/46.3; 548/142

[56] References Cited

U.S. PATENT DOCUMENTS

| | | | |
|---|---|---|---|
| 4,301,019 | 11/1981 | Horodysky et al. | 548/142 |
| 4,382,869 | 5/1983 | Horodysky et al. | 548/142 |
| 4,906,393 | 3/1990 | Farng et al. | 252/47.5 |
| 4,908,144 | 3/1990 | Davis et al. | 252/47.5 |
| 4,935,157 | 6/1990 | Karol | 252/47.5 |

*Primary Examiner*—Prince Willis, Jr.
*Assistant Examiner*—Jerry D. Johnson
*Attorney, Agent, or Firm*—Alexander J. McKillop; Charles J. Speciale; Howard M. Flournoy

[57] ABSTRACT

Mixed alcohol/dimercaptothiadiazole-derived hydroxy borates have been found to be effective antiwear/antioxidant multifunctional additives for lubricants.

23 Claims, No Drawings

MIXED ALCOHOL/DIMERCAPTOTHIADIAZOLE-DERIVED HYDROXY BORATES AS ANTIOXIDANT/ANTIWEAR MULTIFUNCTIONAL ADDITIVES

CROSS-REFERENCE

This application is related to co-pending application Ser. No. 292,168 filed Dec. 30, 1988, entitled "MIXED PHENOL/DIMERCAPTOTHIADIAZOLE-DERIVED HYDROXYTHIOETHER BORATES AS ANTIOXIDANT/ANTIWEAR MULTIFUNCTIONAL ADDITIVES".

BACKGROUND OF THE INVENTION

This application is directed to lubricant compositions containing small additive concentrations of alcoholic/-dimercaptothiadiazole-derived hydroxy borates which possess excellent antioxidant properties as well as very good antiwear and extreme pressure/load carrying characteristics.

The use of alcoholic borate compositions such as borated alkane diols is well known for its friction-modifying properties in a variety of lubricant and grease application, e.g., U.S. Pat. No. 4,615,827.

The use of 2,5-dimercapto 1,3,4-thiadiazole and its derivatives has found widespread application as multifunctional lubricant anticorrosion, antiwear, antioxidant and copper passivation additives, see U.S. Pat. Nos. 4,661,273 and 4,584,114.

The use of borate esters has been widely reported as having beneficial multifunctional and friction reducing properties. For example borates and borate esters are disclosed in RE 37,295 and in U.S. Pat. Nos. 4,370,248; 4,298,486 and 4,273,665.

It has now been found that the use of alcoholic/-dimercaptothiadiazole-derived hydroxy borates provides exceptional antioxidant coupled with very good antiwear/EP activity.

SUMMARY OF THE INVENTION

The use of additive concentrations of alcoholic/-dimercaptothiadiazole-derived hydroxy borates in premium quality automotive and industrial lubricants will significantly enhance their stability, and extend the service life as well as reduce wear. The novel compositions is described herein below are useful at low concentrations and do not contain any potentially undesirable metals, phosphorus or chlorine, and can be readily made commercially under favorable economic conditions.

Generally speaking and in accordance with the invention, there are provided (1) a product made by reacting a dimercaptothiadiazole with an alkylene oxide forming a dimercaptothiadiazole-derived alcohol, which is then co-borated with a phenolic alcohol to form the novel mixed borate esters of this invention and (2) a lubricant composition comprising a major amount of an oil of lubricant viscosity or grease prepared therefrom and a minor effective multifunctional amount of said product.

DESCRIPTION OF SPECIFIC EMBODIMENTS

Both the alcoholic moiety and the dimercaptothiadiazole moiety are believed to provide the basis for the synergistic antioxidant activity. The dimercaptothiadiazole-derived hydroxy group is also believed to contribute additional antiwear/EP properties to these novel additives. The boron moieties may additionally contribute significant antifatigue and/or high temperature stabilizing properties to this new class of additives.

All of these beneficial properties are believed to be enhanced as a result of this novel internal synergism. This unique internal synergism concept is believed to be applicable to similar structures containing (a) alcoholic groups, (b) dimercaptothiadiazole-derived hydroxy groups, and (c) borate ester linkages within the same molecule. The products of this patent application show good stability and compatibility when used in lubricant compositions in the presence of other commonly used additives.

In general for example, the products of reaction are prepared as follows: 2,5-dimercapto 1,3,4-thiadiazole (made by the reaction of hydrazine and carbon disulfide commercially available from R. T. Vanderbilt Chemical Co.) was reacted with alkylene oxide to form dimercaptothiadiazole-derived alcohols (eqn. 1). These derived alcohols were then co-borated with alcohols to form mixed borate esters (eqn. 2 or 3), as generally described below:

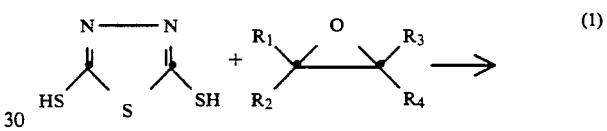

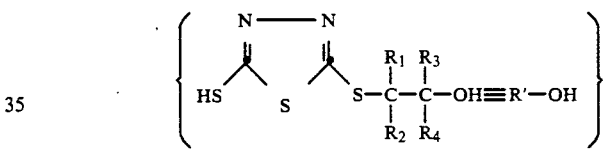

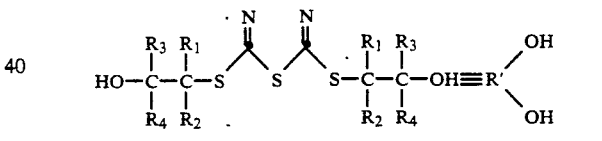

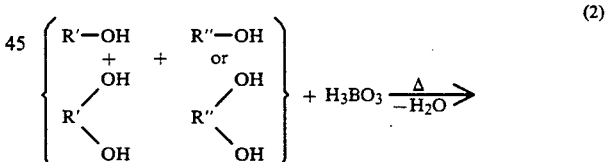

and other structures
where $R_1$, $R_2$, $R_3$, and $R_4$ are hydrogen, or $C_1$ to $C_{60}$ hydrocarbyl.

R' represents the dimercaptothiadiazole-derived moiety.

R'' represents the hydrocarbyl moiety of alcohols or diols ($C_1$ to $C_{60}$ hydrocarbyl or

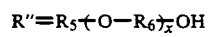

where $R_5$ is $C_6$ to $C_{30}$ hydrocarbyl.
where $R_6$ is $C_2$ to $C_{30}$ hydrocarbyl, preferably $C_2$–$C_6$
X is an integer 1–20
Y and Z are integers and $Y+Z=3$.

An excess of one reagent or anther can be used. Molar quantities, less than molar quantities or more than molar quantities of a boronating agent can be used. Boric acid can be used as a boronating agent or metaborates, trialkyl borates or any other suitable boronating agent may be employed.

Any appropriate mercapto-thiadiazole may be used herein. However, preferred is 2,5-dimercapto-1,3,4-thiadiazole. Some suitable examples include but are not limited to 3,4-dimercapto-1,2,5-thiadiazole, 3,5-dimercaptobenzo 1,2,3-thiadiazole, 4,7-dimercaptobenzo 1,2,3-thiadiazole, 4,6-dimercaptobenzol 1,2,3-thiadizaole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole.

Suitable alkylene oxides are of the formula described in Equation 1 above. Preferred is 1,2-epoxybutane. However, included within the scope of the epoxides as set forth in Equation 1 are 1,2-epoxydecane, 1,2-epoxydodecane, 1,2-epoxytetradecane, 1,2-epoxypentadecane, 1,2-epoxyhexadecane, 1,2-epoxyheptadecane, 1,2-epoxyoctadecane, 1,2-epoxyeicosane, 1,2-epoxybutane and mixtures of such epoxides.

Hydrocarbyl as used herein includes but is not limited to alkyl, aryl, alkaryl, aralkyl, alkenyl cycloalkyl or cycolakenyl groups containing from 8 to 30 carbon atoms, preferably 10 to 22 carbon atoms.

An excess of one reagent or another can be used. Molar quantities, less than molar quantities or more than molar quantities of a boronating agent can be used.

The reactions can, broadly be carried out over a wide range of temperatures from about 50° C. to about 300° C. in from about 0.5 an hour to about 10 hours, depending on temperature and reactivity of the reactants. For specific reactions, the temperatures of reaction can be from about 50° C. to about 250° C., preferably about 100° C. to about 200° C. for the reaction between the DMTD and the alkylene oxide.

When carrying out the reaction between the DMTD derived alcohols and the mixed alcohols and the boronating agent the temperature will generally be from about 100° C. to about 300° C., preferably about 150° C. to about 275° C. Times will run from about one hour or less to about ten (10) hours. However, the boration can be carried out in any convenient manner or sequence and under any conditions known in the art.

Solvents are preferred in carrying out the invention. Broadly, any solvent can be used that does not react and is a solvent for all the reactants and the reaction product and can be removed easily or is compatible with the environment in which the product will be used. Hydrocarbon solvents such as toluene, benzene, xylenes are preferred for the reactions.

The borating agent can be boric acid or a compound of the formula

$$(RO)_p(BO_2)_qZrY$$

where R, Y and Z are hydrogen or alkyl groups of from 1 to about 6 carbon atoms, p and r are 0 to 2 and q is 1 to 3. The useful boronating compounds covered by the above formula include boric acid, metaboric acid, alkyl metaborates, alkyl boroxines, boroxine boroxides, and the like, as well as alkyl and trialkyl borates. Nevertheless, any suitable boronating agent may be used. Preferably the boration is carried out in substantially stoichiometric ratios of reactants. However, an excess of boronating agent is on occasion desirable.

The mixed alcohols are preferably aliphatic alcohols as defined hereinabove in equation (2). Furthermore, in accordance with equation 2, the alcohols may be hydrocarbyl alcohols, saturated and unsaturated, alkane diols and alkoxylated alcohols or mixtures thereof. However, any suitable alcohol may be used herein as for example mixed $C_8$–$C_{20}$ alcohols, saturated and unsaturated, i.e., dodecanol-pentadecanoldecanol, mixtures of hexadecanol, oleyl alcohol, triethoxylated mixed dodecanol-pentadecanol and the like can also be used.

While the reaction sequence has been disclosed to be reaction of (1) a dimercaptothiadiazole and mixed alcohol and (2) a boronating compound, the invention is not limited to that method sequence. The boronation may take place at any convenient point. Furthermore, all reactants can be mixed and reacted in one step, in which case the temperature again can be from about 50° C. to about 300° C. and the time from about 0.5 hour to about ten (10) hours.

The products of the invention are used in minor multifunctional antioxidant/antiwear or anticorrosion amounts with a major proportion of a lubricating oil or grease. In general, this will amount to from about 0.25% to about 15% by weight of the total composition. Furthermore, other additives, such as other detergents, antioxidants, antiwear agents and the like may be present. These can include phenates, sulfonates, succinimides, zinc dithiophosphates, polymers, calcium and magnesium salts and the like.

A most important feature of the invention is the ability of the additive to improve the resistance to oxidation of oleaginous materials such as lubricating oils, either a mineral oil or a synthetic oil, or mixtures thereof, or a grease in which any of the aforementioned oils are employed as a vehicle. In general, mineral oils, both paraffinic, naphthenic and mixtures thereof, employed as a lubricating oil or as the grease vehicle, may be of any suitable lubricating viscosity range, as for example, for about 45 SSR at 100° F. to about 6000 SSU at 100° F., and preferably from about 50 to about 250 SSR at 210° F. These oils may have viscosity indexes ranging to about 100 or higher. Viscosity indices from about 70 to about 95 are preferred. The average molecular weights of these oils may range from about 250 to about 800. Where the lubricant is to be employed in the form of a grease, the lubricating oil is generally employed an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, including calcium or lithium soaps which include calcium or lithium stearates or calcium or lithium hydroxystearates. These are dispersed in the lubricating vehicle in grease-forming quantities in the amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

As noted hereinabove, the lubricants contemplated for use with the products herein disclosed include mineral and synthetic hydrocarbon oils or lubricating viscosity, mixtures of mineral oils and synthetic oils, including mixtures. The synthetic hydrocarbon oils include long-chain alkanes such as cetanes and olefin polymers such as oligomers of hexene, octene, decene, and dodecene, etc. The products of this invention are especially effective in synthetic oils formulated using mixtures of synthetic hydrocarbon olefin oligomers and lesser amounts of hydrocarbyl carboxylic ester fluids. Other synthetic oils, which can be mixed with a mineral or synthetic hydrocarbon oil, include (1) fully esterified ester oils, with no free hydroxyls, such as pentaerythritol esters of monocarboxylic acids having 2 to 20 carbon atoms, timethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

Having described the invention with reference to its broader aspects, the following are offered to specifically illustrate it. It will be understood that the Examples are for illustration only and are not intended to limit the scope of the invention.

EXAMPLE 1

Dimercaptothiadiazole - Vikolox 16 Reaction Adduct

Approximately 37.5 grams of 2,5-dimercapto 1,3,4-thiadiazole (2.25 mole commercially obtained from R. T. Vanderbilt Chemical Company) 134 grams of Vikolox 18 (0.5 mole commercially obtained from Viking Chemical company as $C_{18}$ epoxidized alpha olefin with minimum oxirane 5.4% and general formula $C_{18}H_{36}O$), were suspended in about 100 milliliters of toluene in a 500 milliliter flask. The reactants were slowly heated at 45° C. to trigger the exothermic reaction, and then they were heated at reflux toluene temperature for five hours. Thereafter, the volatiles were removed by vacuum distillation to produce about 171 grams of a viscous, brown waxy material.

EXAMPLE 2

Mixed Neodol 25,3/Dimercaptothiodiazole-derived Hydroxy Borates

Approximately 171 grams of the above product of Example 1, 168 grams of triethoxylated mixed dodecanol-pentadeconal obtained from Shell Chemical Company as Neodol 25-3), 30.9 grams boric acid (0.5 mole), 200 milliliters of toluene were mixed together in a one-liter, four-neck reactor equipped with thermometer, $N_2$ sparger, and Dean-Stark trap condenser and agitator. This mixture was refluxed at boiling toluene over a course of six hours, and water was collected in the Dean-Stark trap. Thereafter, the unreacted solids were filtered off and the organic filtrate was concentrated by removal of all the volatiles through distillaton to level about 348 grams of viscous, brown waxy material.

The mixed borates were blended into mineral oils and evaluated for antioxidant performance by Catalytic Oxidation Test at 325° F. for 40 hours (Table 1); Catalytic Oxidation Test at 325° F. for 72 hours (Table 1).

Catalytic Oxidation Test

Basically, the test lubricant is subjected to a stream of air which is bubbled through at the rate of five liters per hour respectively at 325° F. for 40 hours and at 375° F. for 24 hours. Present in the composition are samples of metals commonly used in engine construction, namely, iron, copper, aluminum, and lead. See U.S. Pat. No. 3,682,980, incorporated herein by reference, for further details of the test.

TABLE 1

| Item | Catalytic Oxidation Test (325° F., 40 hrs.) | | | (375° F., 72 hours) | | |
|---|---|---|---|---|---|---|
| | % change in Viscosity Δ KV | change in acid number Δ TAN | lead loss (mg) | % change viscosity Δ KV | change in acid number Δ TAN | lead loss (mg) |
| Base Oil (200 solvent refined neutral oil paraffinic neutral oil) | 232 | 15.3 | 237 | 4044.3 | 17.9 | 446 |
| 1% of Example 2 in above base oil | 43.1 | 2.13 | 0 | 66.1 | 4.76 | 0 |

The mixed borates were also evaluated for antiwear performance using the Four-Ball Test in minerals oils the Four-Ball Wear Test using a 60 kg load at 200° F., 2000 rpm for thirty minutes as shown in Table 1.

Four-Ball Wear Test

Three stationary balls are placed in the lubricant cup and the lubricant containing the compound to be tested is added thereto, and a fourth ball is placed in a chuck mounted on a device which can be used to spin the ball at known speeds and loads. The samples were tested using ½ inch stainless steel balls of 52100 steel for 30 minutes. K (as reported in Table 2) the wear coefficient is calculated from the wear volume of the stationary ball. The wear volume, V, is calculated from the wear scar diameter D in mm as follows.

$$V = [15, 5\ D^3 - 0.00103L]D \times 10^3\ mm^3$$

where L is the machine load in kg. This equation considers the elastic deformation of the steel balls.

Wear Coefficient K

Dimensionless K is defined as $K = VH/dN$ where
$V$ = wear volume, $mm^3$
$H$ = hardness 9725 $kg/mm^2$ for 52100 steel)

d=(23.3 mm/rev) (RPH×Time)
W=(0.408) (Load in Kg)

TABLE 2

| Example | Four-Ball Wear Test (2000 rpm, 60 kg load, 30 minutes - 200° F.) | |
|---|---|---|
| | Wear Scar Diameter (mm) | Wear Coefficient K (×$10^8$) |
| Base oil (80% solvent paraffinic bright, 20% solvent paraffinic neutral mineral oils) | 3.289 | 3830 |
| 1% Example 2 in above Base Oil | 0.788 | 11.6 |

As shown above, the products of this invention show considerable antiwear and antioxidant activity.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A product of reaction made by reacting at temperatures varying from about 50 to about 250° C. (1) a dimercaptothiadiazole of the formula:

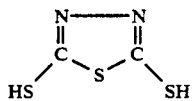

with (2) an alkylene oxide of the formula:

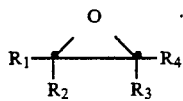

where $R_1$, $R_2$, $R_3$, $R_4$ are each independently H, or $C_1$ to about $C_{60}$ hydrocarbyl, said hydrocarbyl optionally containing S, N, and/or O, thereby forming dimercaptothiadiazole-derived alcohols of general formula:

     (a)

where R' represents the dimercaptothiadiazole-derived moiety and n=1-2; and (3) borating, at temperatures varying from about 100 to about 300° C., an alcoholic mixture comprising said (a) dimercaptothiadiazole derived alcohols and (b) an alcoholic compound or mixtures of compounds of general formula:

     (b)

where R" represents the hydrocarbyl moiety of the alcohol and is $C_1$ to $C_{60}$ hydrocarbyl or R"=$R_5$—(—O—$R_6$—)$_x$—OH where $R_5$ is $C_6$ to $C_{30}$ hydrocarbyl, where $R_6$ is $C_2$ to $C_{30}$ hydrocarbyl, x is an integer from 1-20 and n=1-2, with a suitable boronating agent in substantially equimolar or more than equimolar amounts of the boronating agent to the alcohol compounds.

2. The product of claim 1 wherein the boronating agent is selected from the group consisting of boric acid and a compound of the formula

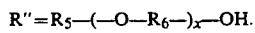

wherein R, Y and Z are individually hydrogen or alkyl groups of from 1 to about 6 carbon atoms, p and r each separately 0 to 2 and q is 1 to 3.

3. The product of claim 2 wherein the boronating agent is boric acid.

4. The product of claim 1 wherein the alcoholic compound is a mixture of dodecanol and pentadecanol.

5. The product of claim 1 wherein the alcoholic compound is a mixture of $C_1$ to about a $C_{60}$ saturated alcohols.

6. The product of claim 1 wherein the alcoholic compound is a mixture of $C_1$ to about a $C_{60}$ unsaturated alcohols.

7. The product of claim 1 wherein the alkylene oxide is a $C_{18}$ epoxidized alpha olefin.

8. The product of claim 1 wherein the alcoholic compound is a mixture of $C_{12}$-$C_{15}$ alcohols.

9. The product of claim 1 wherein the alcoholic compound is a diol.

10. The product of claim 1 wherein the alcoholic compound has the general structure R"=$R_5$—(—O—$R_6$—)$_x$—OH.

11. A lubricant composition comprising a major proportion of a lubricating oil or grease prepared therefrom and an effective multifunctional antioxidant and antiwear/EP amount of a product of reaction made by reacting at temperatures varying from about 50° to about 250° C. (1) a dimercaptothiadiazole of the formula:

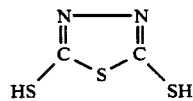

with (2) an alkylene oxide of the formula:

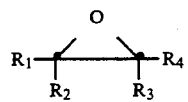

where $R_1$, $R_2$, $R_3$, $R_4$ are each independently H, or $C_1$ to about $C_{60}$ hydrocarbyl, said hydrocarbyl optionally containing S, N, and/or O, thereby forming dimercaptothiadiazole-derived alcohols of general formula:

     (a)

where R' represents the dimercaptothiadiazole-derived moiety and n=1-2; and (3) borating, at temperatures varying from about 100° to about 300° C., an alcoholic mixture comprising said (a) dimercaptothiadiazole derived alcohols and (b) an alcoholic compound or mixtures of compounds of general formula:

     (b)

where R" represents the hydrocarbyl moiety of the alcohol and is $C_1$ to $C_{60}$ hydrocarbyl or R"=$R_5$—(—O—$R_6$—)$_x$—OH where $R_5$ is $C_6$ to $C_{30}$ hydrocarbyl, where $R_6$ is $C_2$ to $C_{30}$ hydrocarbyl, N is an integer from 1-20 and n=1-2, with a suitable boronating agent in substantially equimolar or more than equimolar amounts of boronating agent to the alcohol compounds.

12. The composition of claim 11 wherein the boronating agent is selected from the group consisting of boric acid and a compound of the formula $$(RO)_p(BO_2)_q ZrY$$

wherein R, Y and Z are hydrogen or alkyl groups of from 1 to about 6 carbon atoms and p and r are each individually 0 to 2 and q is 1 to 3.

13. The composition of claim 12 wherein the boronating agent is boric acid.

14. The composition of claim 11 wherein the alcoholic compound is a mixture of $C_8$ to $C_{20}$ saturated alcohols.

15. The composition of claim 14 wherein the alcoholic compound is a mixture of $C_{12}$–$C_{16}$ alcohols.

16. The composition of claim 15 wherein the alcoholic compound is a mixture of dodecanol and pentadecanol.

17. The composition of claim 11 wherein the alkylene oxide is a $C_{18}$ epoxidized alpha olefin.

18. The composition of claim 11 wherein the lubricant is an oil of lubricating viscosity, selected from the groups consisting of (1) mineral oils, (2) synthetic oil or a mixture of synthetic oils, (3) mixture of (1) and (2) or (4) a grease prepared from any one of (1), (2), or (3).

19. The composition of claim 18 wherein said oil is a mineral oil.

20. The composition of claim 18 wherein said oil is a synthetic oil.

21. The composition of claim 18 wherein the lubricant is a grease.

22. The composition of claim 11 wherein the alcoholic compound is an alkane diol.

23. The composition of claim 11 wherein the alcoholic compound has the general structure $$R'' = R_5-(-O-R_6-)_x-OH.$$

* * * * *

UNITED STATES PATENT AND TRADEMARK OFFICE
CERTIFICATE OF CORRECTION

PATENT NO. : 5,137,649

DATED : August 11, 1992

INVENTOR(S) : Liehpao O. Farng et al.

It is certified that error appears in the above-identified patent and that said Letters Patent is hereby corrected as shown below:

Column 8, line 66, "N" should read --X--.

Signed and Sealed this

Twenty-eighth Day of September, 1993

Attest:

BRUCE LEHMAN

Attesting Officer

Commissioner of Patents and Trademarks